US012740754B2

(12) United States Patent
Black et al.

(10) Patent No.: US 12,740,754 B2
(45) Date of Patent: Sep. 22, 2026

(54) QUICK HEAD DISCONNECT FOR X-RAY IMAGING SYSTEM

(71) Applicant: 3DIO, Inc., Orem, UT (US)

(72) Inventors: Kolby Black, Salem, UT (US); Brad Allen, Orem, UT (US)

(73) Assignee: 3DIO, INC., Orem, UT (US)

( * ) Notice: Subject to any disclaimer, the term of this patent is extended or adjusted under 35 U.S.C. 154(b) by 79 days.

(21) Appl. No.: 18/422,545

(22) Filed: Jan. 25, 2024

(65) Prior Publication Data

US 2025/0247938 A1 Jul. 31, 2025

(51) Int. Cl.

| | |
|---|---|
| ***A61B 6/02*** | (2006.01) |
| ***A61B 6/00*** | (2006.01) |
| ***A61B 6/51*** | (2024.01) |
| ***H05G 1/06*** | (2006.01) |

(52) U.S. Cl.

CPC .......... *A61B 6/4411* (2013.01); *A61B 6/4458* (2013.01); *A61B 6/56* (2013.01); *H05G 1/06* (2013.01); *A61B 6/025* (2013.01); *A61B 6/512* (2024.01)

(58) Field of Classification Search

None

See application file for complete search history.

(56) References Cited

U.S. PATENT DOCUMENTS 1,556,917 A * 10/1925 Dee .......................... H05G 1/02 378/197
5,283,823 A * 2/1994 Morris ................. A61B 6/4405 378/198
5,553,115 A * 9/1996 Odaka .................. A61N 5/1049 378/170
5,781,610 A * 7/1998 Miles ....................... H05G 1/42 378/168
6,431,751 B1 * 8/2002 Everett ................ A61B 6/4233 378/197
7,278,784 B2 * 10/2007 Hack ...................... A61B 6/512 378/191
9,649,078 B2 * 5/2017 Joshi ...................... A61B 6/107
10,849,579 B2 * 12/2020 Turner ................. A61B 6/4405

(Continued)

FOREIGN PATENT DOCUMENTS

JP 2013128593 A * 7/2013 ............. A61B 6/588

*Primary Examiner* — Thomas R Artman

(74) *Attorney, Agent, or Firm* — Kenneth E. Horton; Barnes & Thornburg LLP

(57) ABSTRACT

X-ray imaging systems containing a quick disconnect feature for the X-ray head containing the X-ray source are described. The X-ray imaging systems comprise an X-ray head containing an X-ray source and supporting electronics including high-voltage electronics, a control device, an arm coupled to the X-ray head, and low voltage cabling disposed within the arm and configured to connect the supporting electronics to the control device, the electrical cabling comprising a disconnect between the supporting electronics and the control device, and where the X-ray head is removably attached to the arm so that when the electrical cabling is disconnected, the X-ray head can be removed from the X-ray system. These X-ray imaging systems offer an easier method for removing the X-ray head, such as for replacement, servicing, and/or repair. Other embodiments are described.

15 Claims, 12 Drawing Sheets

(56) References Cited

U.S. PATENT DOCUMENTS

| | | | | |
|---|---|---|---|---|
| 11,701,072 | B2 * | 7/2023 | Liu | A61B 6/4411 378/101 |
| 12,285,279 | B2 * | 4/2025 | Subramanyan | A61B 90/39 |
| 2006/0067463 | A1 * | 3/2006 | Hack | A61B 6/512 378/38 |
| 2016/0081173 | A1 * | 3/2016 | Lee | H05G 1/06 378/101 |
| 2017/0027532 | A1 * | 2/2017 | Joshi | A61B 6/586 |
| 2020/0163634 | A1 * | 5/2020 | Turner | A61B 6/4441 |
| 2022/0151576 | A1 * | 5/2022 | Subramanyan | A61B 6/5205 |
| 2022/0369446 | A1 * | 11/2022 | Liu | A61B 6/4007 |
| 2025/0247938 | A1 * | 7/2025 | Black | A61B 6/4411 |

* cited by examiner

QUICK HEAD DISCONNECT FOR X-RAY IMAGING SYSTEM

FIELD

This application relates generally to X-ray equipment. More specifically, this application relates to X-ray devices and systems that contain a quick disconnect mechanism that allows quick removal/attachment of an X-ray head to/from the X-ray system.

BACKGROUND

X-ray imaging systems, including three dimensional (3D) dental imaging systems, typically contain an X-ray source and an X-ray detector. X-rays (or other types of radiation used for imaging) are emitted from the source and impinge on the X-ray detector to provide an X-ray image of the object or objects that are placed between the X-ray source and the detector. The X-ray detector is often an image intensifier or even a flat panel digital detector. In some configurations, the X-ray source can be contained in an X-ray head (or head) that contains supporting electronics for the X-ray source, including high-voltage electronics.

SUMMARY

This application relates generally to X-ray imaging systems that include a quick disconnect feature for the X-ray head that contains the X-ray source to enable easy removal/attachment of the X-ray head from the rest of the system. The X-ray imaging systems comprise an X-ray head containing an X-ray source and supporting electronics including high-voltage electronics, a control device, an arm coupled to the X-ray head, and low voltage cabling disposed within the arm and configured to connect the supporting electronics to the control device, the electrical cabling comprising a disconnect between the supporting electronics and the control device, and where the X-ray head is removably attached to the arm so that when the electrical cabling is disconnected, the X-ray head can be removed from the X-ray system. These X-ray imaging systems offer an easier method for removing the X-ray head, such as for replacement, servicing, and/or repair, especially if the X-ray head needs to be serviced or repaired at a location remote from the place of use of the X-ray imaging system.

BRIEF DESCRIPTION OF THE DRAWINGS

The following description can be better understood in light of the Figures which show various embodiments and configurations of the X-ray imaging systems described herein.

Figure 1:
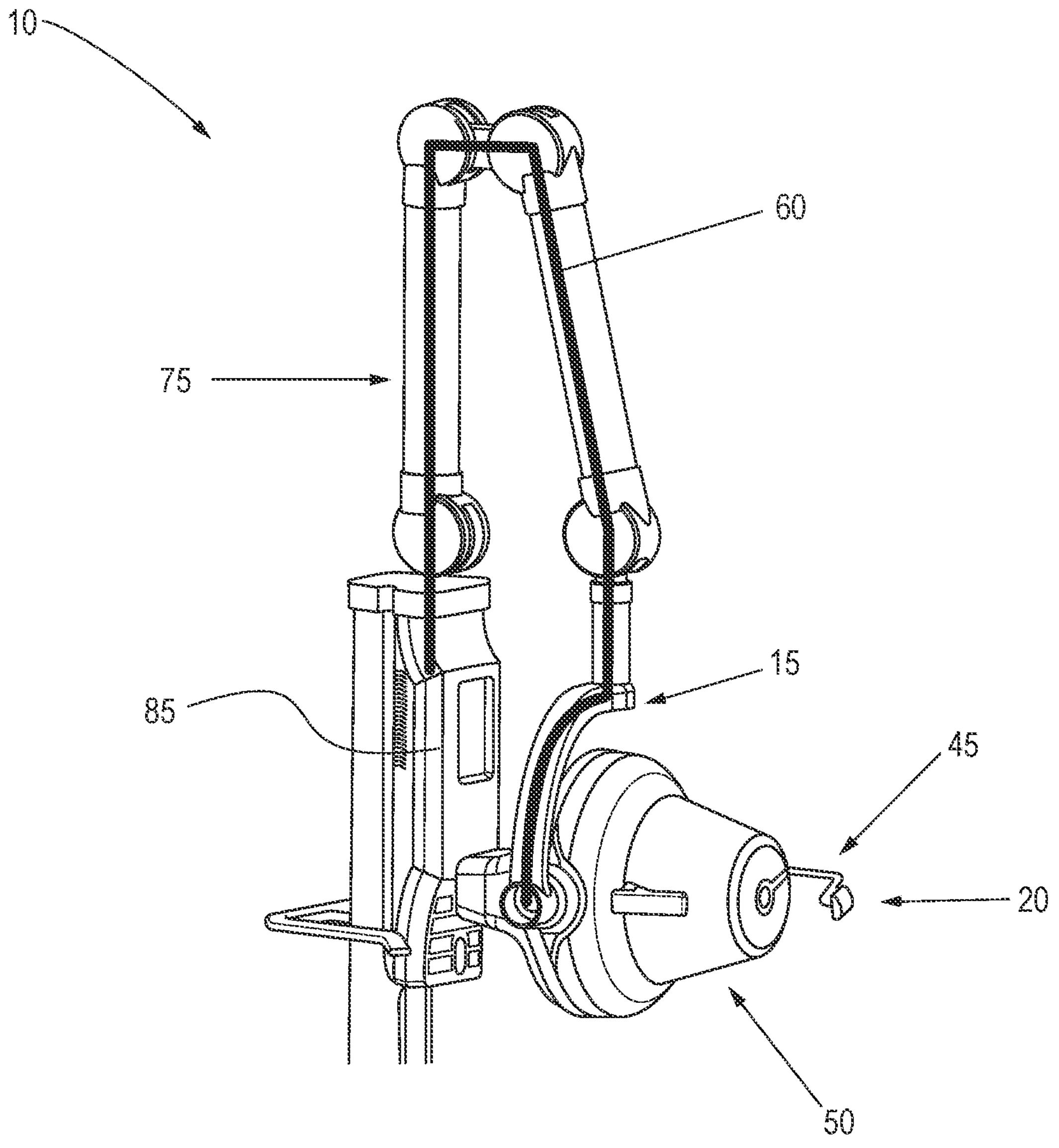
FIG. 1 depicts some embodiments of X-ray imaging systems containing a disconnect feature.

Together with the following description, the Figures demonstrate and explain the principles of the structures and methods described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray systems can be implemented and used without employing these specific details. Indeed, the described systems and methods can be placed into practice by modifying the described systems and methods and can be used in conjunction with any other apparatus and techniques conventionally used in the industry. For example, while the description below focuses on imaging systems for dental imaging, they can be used for other purposes such as medical imaging, veterinary imaging, industrial inspection applications, and anywhere that X-ray radiography equipment is used to generate an X-ray image. It may also apply to any instance where an X-ray source is being used for any general imaging purpose involving X-rays.

In addition, as the terms on, disposed on, attached to, connected to, or coupled to, etc. are used herein, one object (e.g., a material, element, structure, member, etc.) can be on, disposed on, attached to, connected to, or coupled to another object-regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Dental X-ray radiography can be performed by positioning an X-ray source on one side of an object (e. g., a tooth, a set of teeth, a portion or all of the jaw) and causing the X-ray source to emit X-rays through the teeth, soft tissue, and bone toward an X-ray detector (or sensor) located on the other side of the teeth, either inside or outside of the mouth. As the X-rays pass through the teeth, jaws, and other tissues, their energies are absorbed to varying degrees depending on the tissue composition and the total thickness of the tissues. The X-rays arriving at the X-ray detector form a 2D X-ray image based on the cumulative absorption through the teeth, bones and other mouth structures. These intraoral X-ray images provide a high level of detail of the tooth, bone, and supporting tissues. The images also allow users (i.e., dentists) to find cavities, examine tooth roots, evaluate the condition of the bony area around the tooth, determine if periodontal disease is present or a concern, and monitor the status of developing teeth, among other things.

In medical or dental applications of X-ray imaging systems, one of the considerations for the operator (radiologist, or doctor, or other medical specialist) using the system is the ease of maintenance or repair. Traditionally, X-ray imaging systems are complex, heavy, and large because of the requirement for high-voltage electronics and other system design requirements. X-ray imaging systems cannot be used while they are waiting for maintenance or actually being repaired, imposing both costs and inconvenience on the operator and/or the medical/dental practice when the X-ray system is unavailable. So one of the desirable features of any X-ray imaging system is easy and quick maintenance or repair of the X-ray imaging system and/or its major components.

Accordingly, the X-ray imaging systems (or X-ray systems) described herein contain a disconnect feature (or disconnect) to facilitate quick and easy removal of the X-ray head from the remainder of the X-ray system for replacement, servicing, or repair. Some configurations of the X-ray systems are illustrated in FIG. 1. In FIG. 1, an X-ray imaging system 10 can contain an X-ray head 50 that includes an X-ray source 30 (not shown) and high voltage electronics (not shown) that is connected to cabling (or cables) 75. The high voltage electronics can provide typically between about 40,000 volts and about 200,000 volts for most medical applications, and/or about 50,000 volts up to about 70,000 volts for most dental applications, whether DC or AC current. The X-ray imaging systems also contain an arm 60 that is coupled to the X-ray head 50 and to the cabling 75. The low voltage in the cabling 75 can be up to about 1500 volts, but typically can be about 220 volts, about 100 volts, or even about 50 volts, whether AC or DC current.

The cabling 75 can be disposed within or on the arm 60. The cabling 75 can be configured to connect and provide both electrical power and control/data signals to the supporting high voltage electronics coming from a control device 85. The cabling 75 also contains a disconnect feature (or disconnect) configured to disconnect the cabling 75 from the X-ray head 50, enabling separation of the control device and the high voltage electronics within the head. The X-ray head 50 is also removably connected to the arm 60 so that when the cabling 75 is disconnected from the control device 85, the X-ray head 50 containing the high voltage electronics can be removed from the remainder of the X-ray system 10.

The X-ray head 50 can also be connected to an X-ray detector 20. The X-ray detector 20 can contain any detector (or sensor) that detects X-rays, including an image intensifier, CMOS camera, and/or a digital flat panel detector. In some configurations, the detector can have a substantially square or rectangular shape with a length ranging from about 20 cm to about 30 cm. In some configurations, the detector can have a substantially square or rectangular shape with a length ranging from about 1 cm to about 4 cm. In other embodiments, though, the X-ray detector 20 does not need to have a substantially square or rectangular shape. The X-ray detector 20 can be connected to the X-ray head 50 using an aligner 45 that helps keep the X-ray detector 20 properly positioned with respect to the tooth of a patient while a dental X-ray image is taken, or that serves similar functions in medical X-ray applications.

The system 10 can also contain any X-ray source 30 inside the X-ray head 50 that allows the X-ray system 10 to take multiple X-ray images or radiographs. In some embodiments, the X-ray source 30 can contain any type of source that generates and emits short pulses of X-rays, such as those pulses ranging from about 5 to about 7 milliseconds duration up to about 40 to about 60 milliseconds duration. In some embodiments, the X-ray source 30 can include a standard stationary anode X-ray source, micro-focus X-ray source, rotating anode X-ray source, and/or a carbon-nanotube or Spindt-cathode-type X-ray source. In some embodiments, the X-ray source can operate with about 40 to about 90 kV and from about 1 to about 10 mA. In other embodiments, the X-ray source can operate from about 50 kV or about 60 kV to about 65 kV or about 70 kV and with a current ranging from about 2 mA to about 7 mA. In some configurations, the X-ray detector 20 can be synchronized and/or aligned with the X-ray source 30 so that the X-ray system 10 can take multiple images with high image efficiency. This synchronization can be performed by controlling both the X-ray detector and the X-ray source using an internal or external controller, such as a computer, or by configuring the detector to collect data when it first detects X-rays, thereby controlling the timing of the X-ray source needs so it emits the X-ray pulses when desired.

In some embodiments, the X-ray source and X-ray detector can be made modular so that different sizes and types of X-ray sources and X-ray detectors can be used. This allows the X-ray source and the X-ray detector to be easily replaceable in the X-ray system 10.

Figure 9:
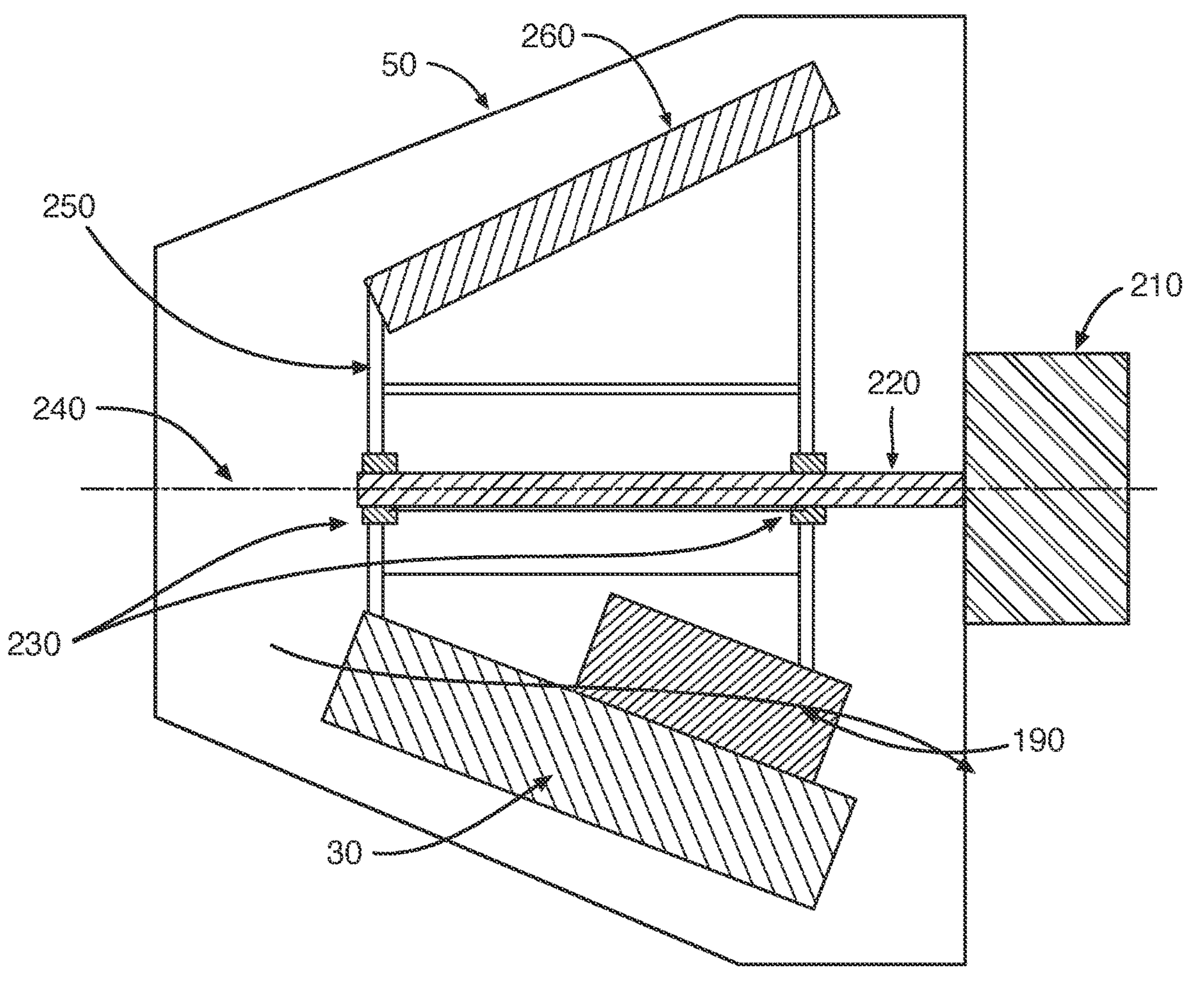
FIGS. 9 and 10 illustrate some embodiments of the X-ray head of an X-ray imaging system.

As shown in detail in FIG. 9, the X-ray source 30 can be contained in X-ray head 50. The X-ray head 50 can be configured with a first part enclosing the X-ray source 30 as shown in FIG. 9. The X-ray head 50 can also contain a second part that contains a counterweight 260 for the X-ray source 30, power electronics 190, and other components and which facilitates smooth vibration-free rotary motion of the X-ray source 30 within the X-ray head 50. The X-ray source 30 and its associated power electronics 190 and the counterweight 260 are located on substantially opposite sides of rotating mechanical assembly 250 which supports the X-ray source 30, the high-voltage power electronics 190, counterweight 260, and other components (not shown). The rotating mechanical assembly 250 is mounted to axle 220 (or other mechanical device to support the mechanical assembly) with an axis of rotation 240 using the bearings and/or electric motor assembly 230 to enable and drive rotation of the mechanical assemble 250.

As shown in FIG. 9, the X-ray head 50 can be configured so that it is a single part that encloses both the X-ray source 30 and these components. In other configurations, the housing can be separated into different parts to contain the X-ray source 30 and other components. As shown in FIG. 9, the electronic components for control and high-voltage power conditioning 210 can alternatively be located just outside of the X-ray head 50. In other embodiments, these electronic components 210 can be located on the support arm or other convenient location. In yet other embodiments, these electronic components 210 can be located internal to the X-ray head 50.

Figure 10:
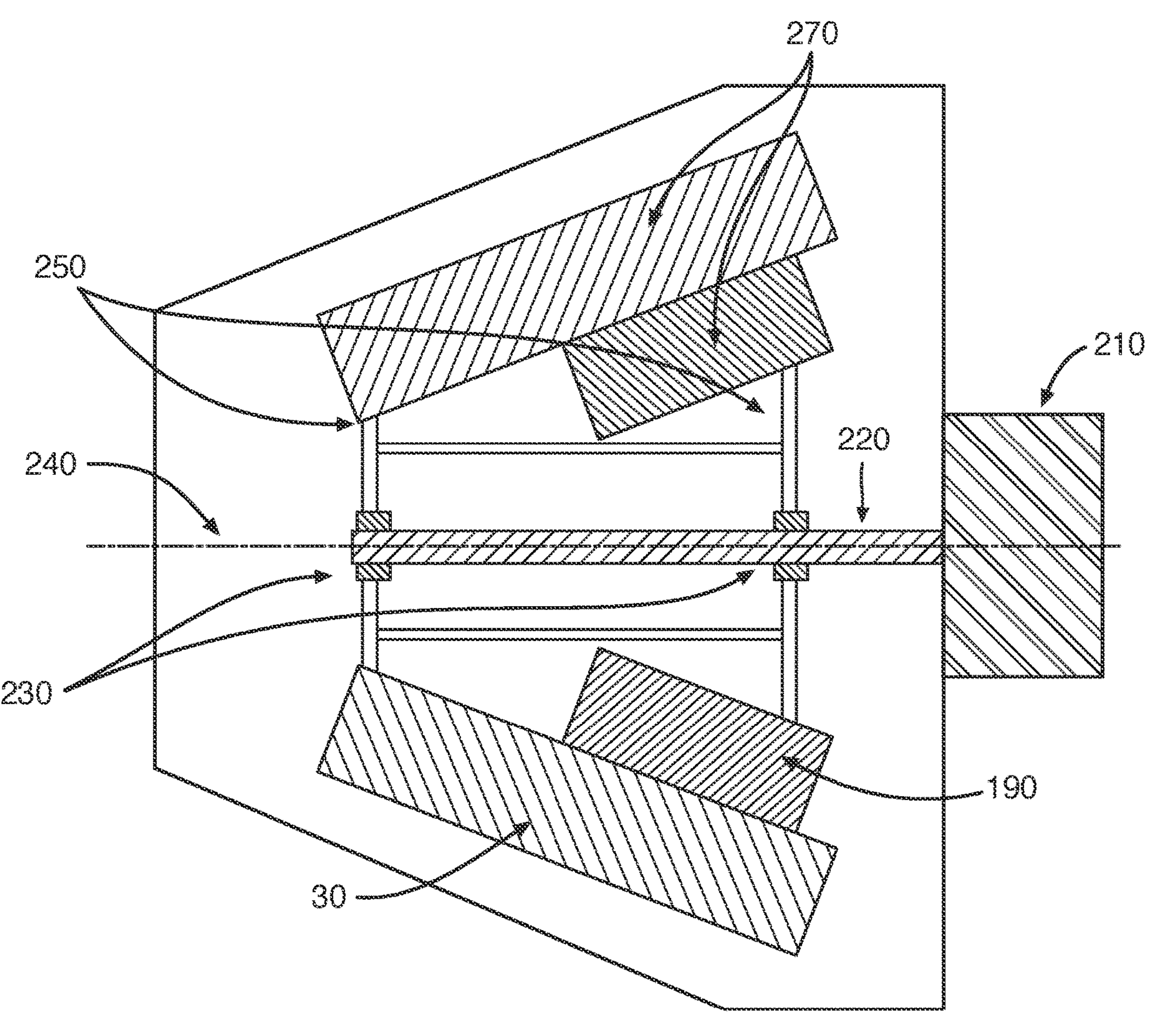

In some embodiments, multiple X-ray sources can be used in the X-ray imaging systems. In these embodiments, as shown in FIG. 10, multiple X-ray sources (30, 270) would enable various performance advantages such as a reduction in the mechanical rotation speed required to cover all of the desired source positions needed to generate a 3D image. These X-ray sources could be fired in an alternating manner or otherwise as required to obtain all of the desired 2D images from the various X-ray source locations within the head. The remainder of the components in FIG. 10 can be similar to those shown in FIG. 9, with the exception that the second X-ray source and its associated high voltage electronics 270 have replaced the counterweight 260.

In some configurations, the X-ray system 10 can contain a removable power source (such as a battery) and optionally a power supply. In these configurations, the power source and the power supply can be located internal to the housing of the X-ray head 50. The supporting electronics for the high-voltage power source and the power supply, as well as the supporting electronics for handling the image data for buffering, wifi transmission, or other data-transmission functionality, can also be located internal to the X-ray head 50. Thus, in these configurations, the X-ray system 10 does not contain an external power cord. Incorporating the power source (i.e., the battery), the power supply, and the high voltage electronics all within the X-ray head 50 may allow various design benefits that will depend on the application.

Figure 11:
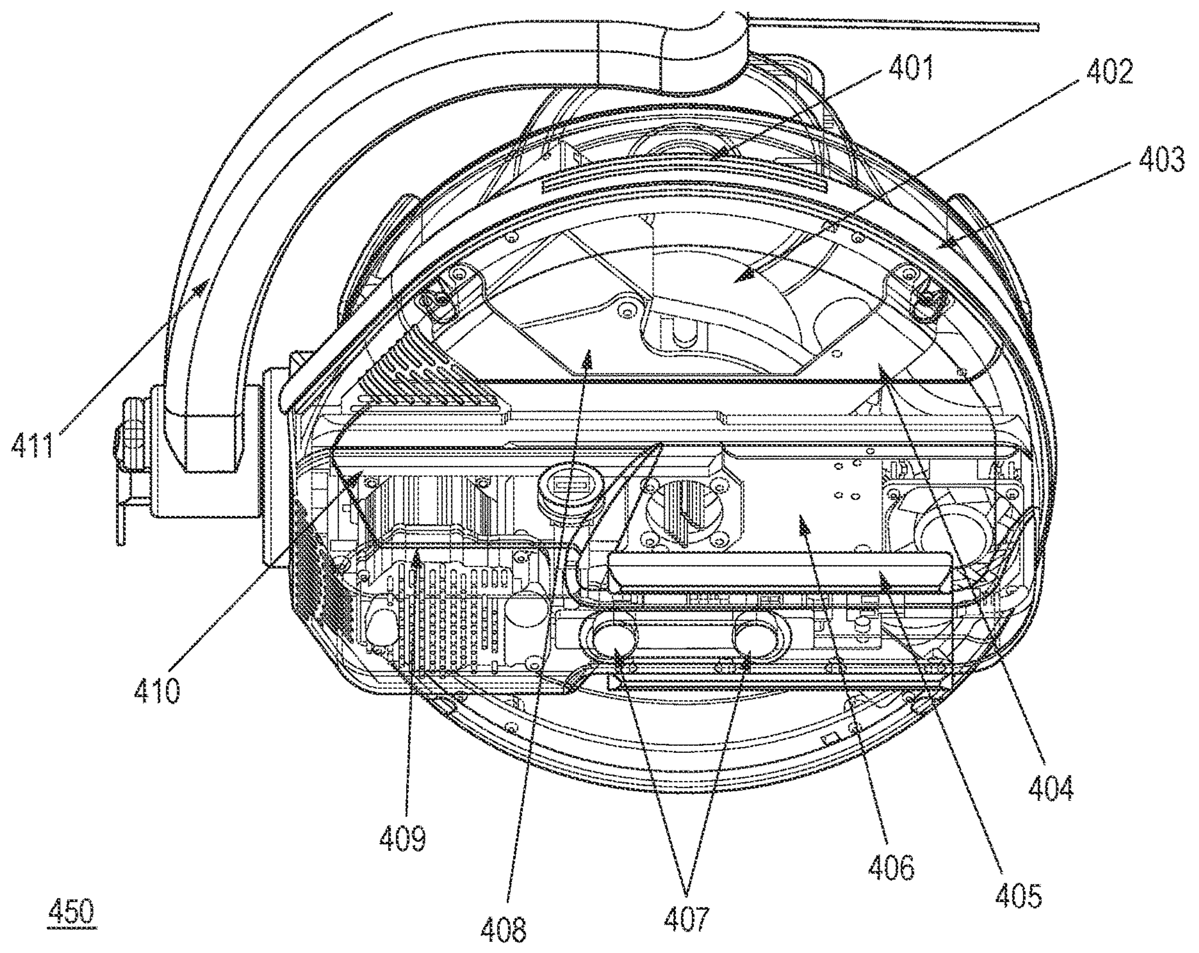
FIG. 11 illustrates other embodiments of the X-ray head of the X-ray imaging systems.

Other configurations of the X-ray head 450 are illustrated in FIG. 11. In these configurations, the X-ray head contains lights 401, slip ring 402, cover support ring 403, internal cover supports 404 and 406, handles 405, transport magnets 407, stage 408, motor 409, support 410, and yoke 411. The lights 401 comprise a light-emitting diode (LED) strip on the top and bottom of the X-ray head 450 to show warnings, ready status, and other status information to the user. The slip ring 402 allows rotation of the high voltage electronics without worrying about the cabling getting tangled or needing to unwind. The cover support ring 403 holds the two covers together and contains inserts for the lights 401. The internal cover supports 404/406 are structures providing support to the cover support ring 402 and the covers of the X-ray head 450, as well as holding the fan and IR sensors contained in the X-ray head 450. The internal cover supports 404/406 also reduce the size of the main support beam 410, thereby reducing the size and weight of the head. The handles 405 are used to provide a grip for anyone moving the X-ray head. The transport magnets 407 located in the X-ray head 450 and in the controller (of the control device) can be used as a fastening point or lock to control undesired motion during transport of the system. The stage 408 comprises a structural connection holding the X-ray tube (of the X-ray source) and X-ray power supply. The motor 409 contains the electrical components controlling speed, thereby eliminating the need for an extra circuit board. The main support beam 410 comprises the main structure of the X-ray head 450 and connects to the bottom of the yoke 411, thereby holding the weight of the X-ray head 450. The main support beam 410 only extends to the middle of the X-ray head 450 rather than extending across the entire head, thereby reducing weight. The yoke 411 connects the X-ray head 450 to the arm and allows for the head to swivel or rotate for ease of positioning.

The arm 60 of the X-ray imaging systems 10 can have any configuration that allows the X-ray source 30 in the X-ray head 50 to direct X-ray beams at the desired angle through the tooth (or teeth), soft tissue, and/or bone and on to the X-ray detector 20, while also aiding the operator to move the X-ray head 50 into any desired position to take images of a patient. In the embodiments shown in FIG. 1, the arm 60 has a bent configuration with the X-ray head 50 connected to an end thereof. In other configurations, the arm need not be bent and can have jointed or articulated sections as shown therein. In yet other configurations, the X-ray head 50 can be connected to the arm 60 at any location other than the end as shown in FIG. 1. In yet other configurations, the arm 60 can contain less or more sections that allows the arm 60 to move through a wider range of motions. And the arm 60 can be configured with any length that allows it to be moved into any desired orientation and desired operational space.

The X-ray imaging system 10 can further include a yoke 15 that is connected both to the arm 60 and the X-ray head, as shown in FIG. 1. The X-ray head 50 can be coupled to the arm 60 using the yoke 15 and at least a portion of the cabling 75 can be disposed within the yoke 15. In these configurations, the X-ray head 50 can be further configured to be removed from the yoke 15 such that when the cabling 75 is disconnected from the control device 85, the X-ray head 50 can then be removed from the remainder of the X-ray system 10.

Figure 2:
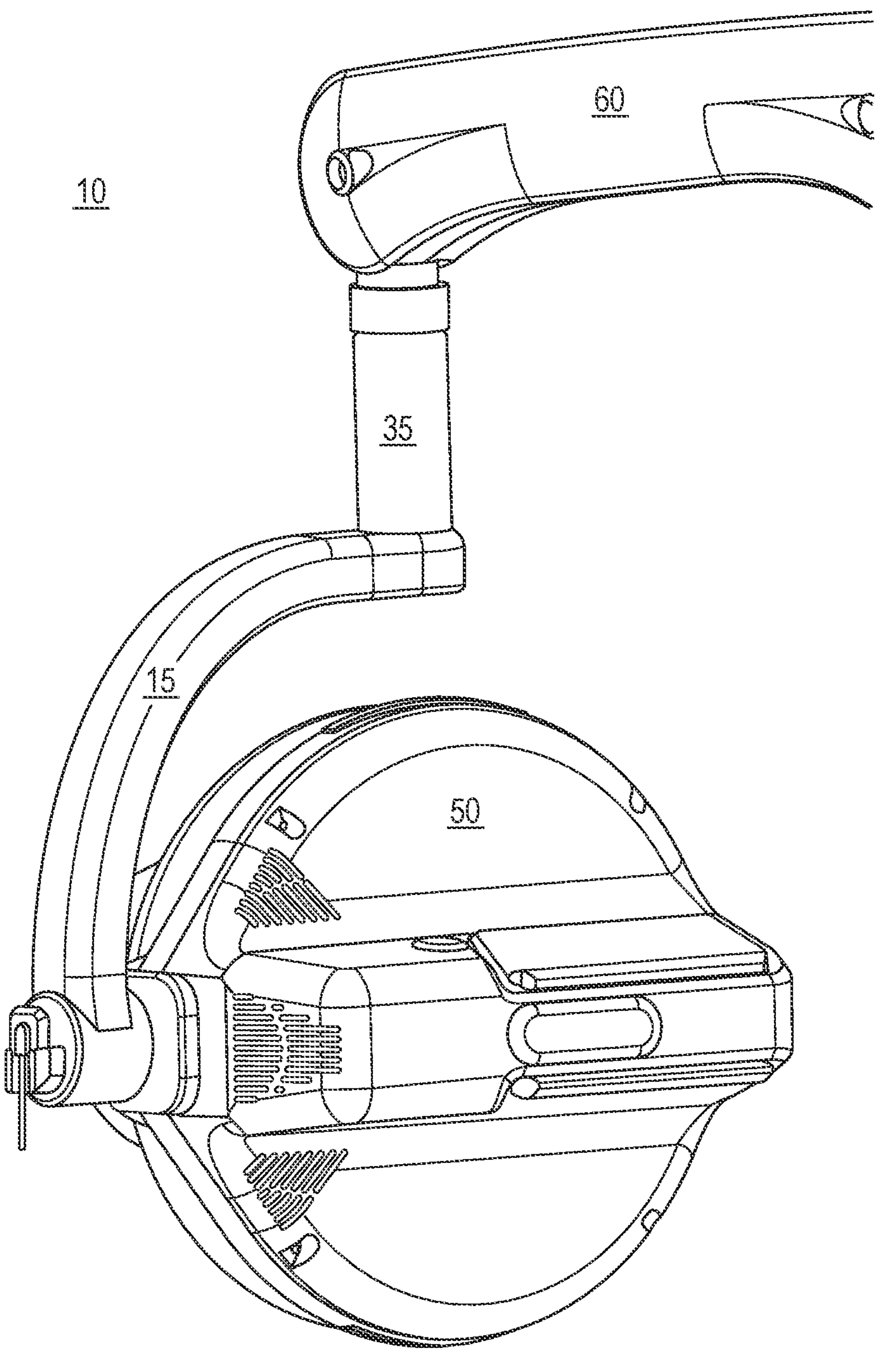
FIG. 2 shows other embodiments of X-ray imaging systems containing a disconnect feature.

Some configurations of the yoke 15 and the arm 60 can be seen in FIG. 2. In these configurations, a first end of the yoke 15 is connected to the X-ray head 50. A second end of the yoke 15 is connected to an arm extension 35 which is, in turn, connected to the arm 60. As explained herein, these configurations of the arm and yoke make use of the disconnect feature quick and easy.

Figure 3:
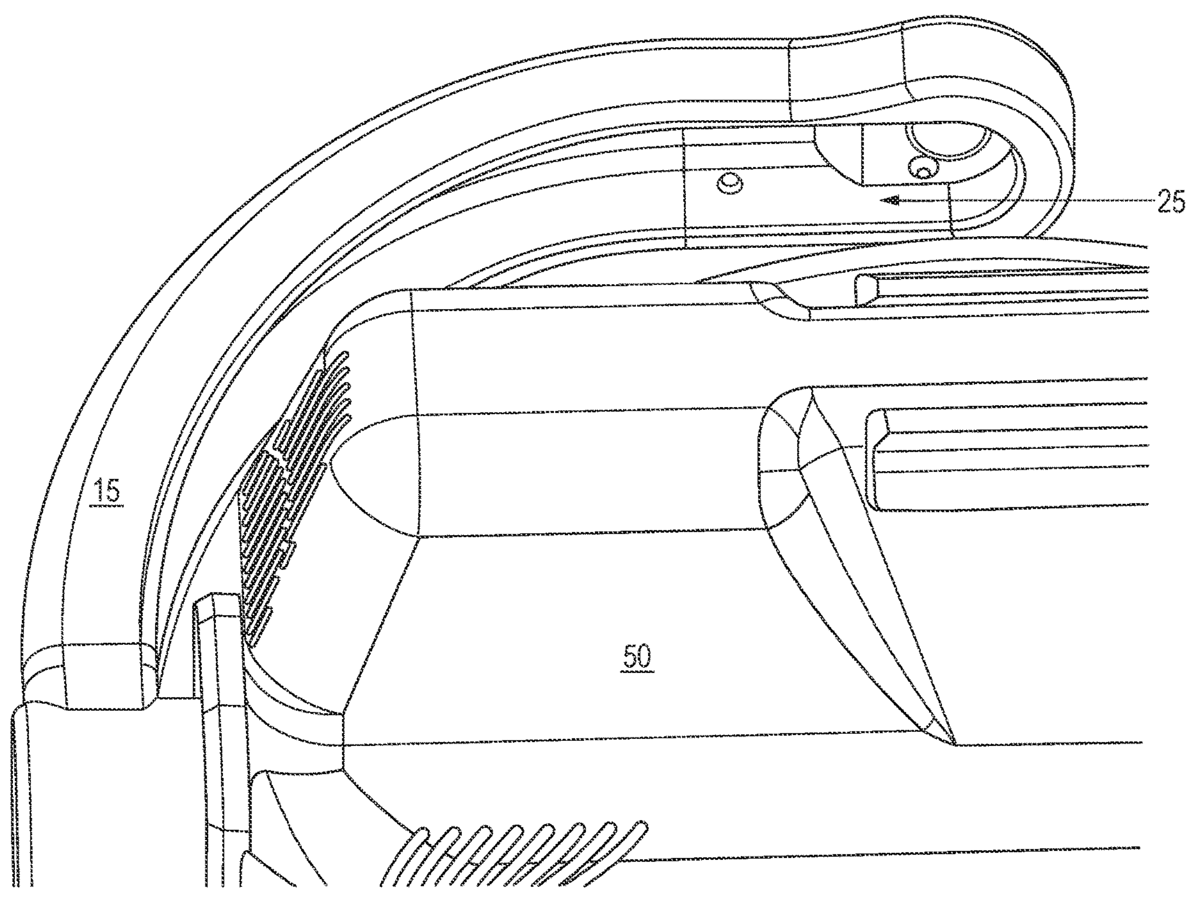
FIG. 3 depicts some embodiments of a yoke in the X-ray imaging systems containing a disconnect feature.

In some embodiments, the yoke 15 can contain an underside 25 that can be configured to enclose the cabling 75 that is located within the yoke 15, as shown in FIG. 3. In other embodiments, the outer surface of the yoke 15 can contain an indentation that can be configured to enclose the cabling 75 that is run along the outside of the yoke. In these embodiments, the arm 60 (including any arm extension) can also be configured so that the cabling 75 can run along the outside of the arm.

In some embodiments, the yoke 15 can configured to be disconnected from the X-ray head 50. In other embodiments, the yoke 15 can configured to be disconnected from the rest of the arm 60, including any arm extension 35 if used. In yet other embodiments, the yoke 15 can be configured to be separable and disconnected from both the X-ray head 50 and the rest of the arm 60.

The disconnect feature can contain any electrical connector that is capable of being connected and disconnected. In some configurations, the electrical connector can fit inside of the arm 60 and/or yoke 15 and can withstand a multitude of connections and disconnections. In some embodiments, the electrical connector can be configured to be located within or on the arm 60. The X-ray system 10 can include multiple electrical connectors along the path of the cabling 75. In some embodiments, each of the one or more electrical disconnects can be configured so that they cannot be mixed up, such as having different types of electrical connectors, or other features that make each connection specific and easily identifiable. In certain aspects, the electrical connector can include a locking system to prevent the cabling 75 from coming loose during operation of the X-ray system 10. Some examples of the electrical connectors that can be used include AC connectors like IEC connectors and NEMA connectors; DC connectors like barrel connectors; RCA connectors; coaxial connectors like BNC connectors and F connectors; fiber optic connectors including SC connectors and LC connectors; and signal cables such as USB, display (HDMI or DisplayPort), ethernet and d-subminiature connectors. In some configurations, any electrical connector, whether custom-designed, or off-the-shelf parts, could be used as long as it meets the requirements for making and breaking the connection as needed with a reasonable case, and also for avoiding any confusion or mix-up when reconnecting the cabling.

In some embodiments, the disconnect can also include a mechanical connector. To make servicing less expensive, the X-ray head 50 can be removable from the remainder of the X-ray system 10 using this mechanical (and electrical)

connector. This mechanical connector could be located where the yoke meets the arm (including any arm extension), where the yoke 15 meets the X-ray head, or at another location that is easy to access by an operator. In some configurations, the mechanical connector can be located in the yoke 15 since there is sufficient room in the yoke 15 to also place the electrical connector. Some examples of the mechanical connectors that can be used in the disconnect feature include bolts and nuts, screws, washers, rivets, pins, clevises, cotter pins, springs, and/or clamps. The X-ray system 10 can include multiple mechanical connectors along the path of the cabling 75. In some embodiments, each of the one or more mechanical connecters can be configured so that they cannot be mixed up, such as having different sizes or configuration of connectors, or other features that make each mechanical connection specific and easily identifiable.

The cabling 75 in the X-ray systems 10 described herein can run from the control device 85, along the arm 60 and yoke 15, and then be connected to the X-ray head 50. The cabling 75 can be difficult to feed in and out of the X-ray head without removing components that limit access to the X-ray head 50. Therefore, a break in the cabling 75 for the electrical connector can be added close to the location where the X-ray head 50 will be mechanically disconnected.

Figure 4:
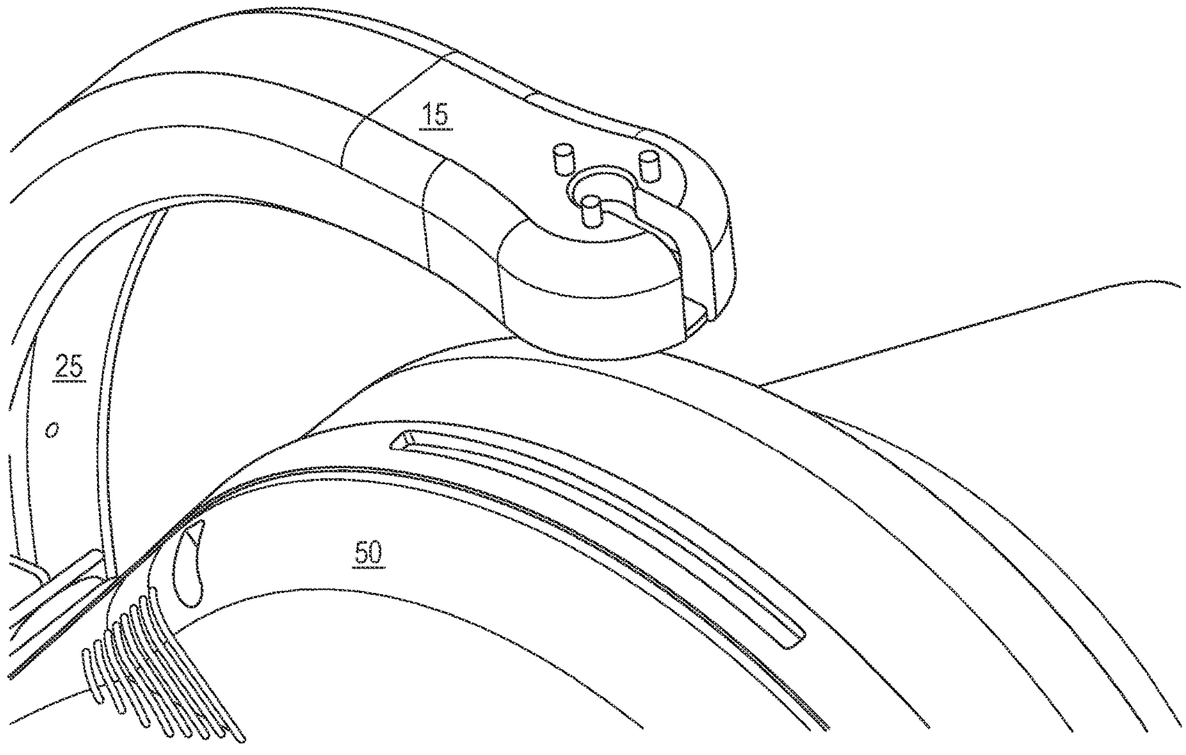
FIGS. 4 and 5 depict other embodiments of a yoke in the X-ray imaging systems containing a disconnect feature.
Figure 5:
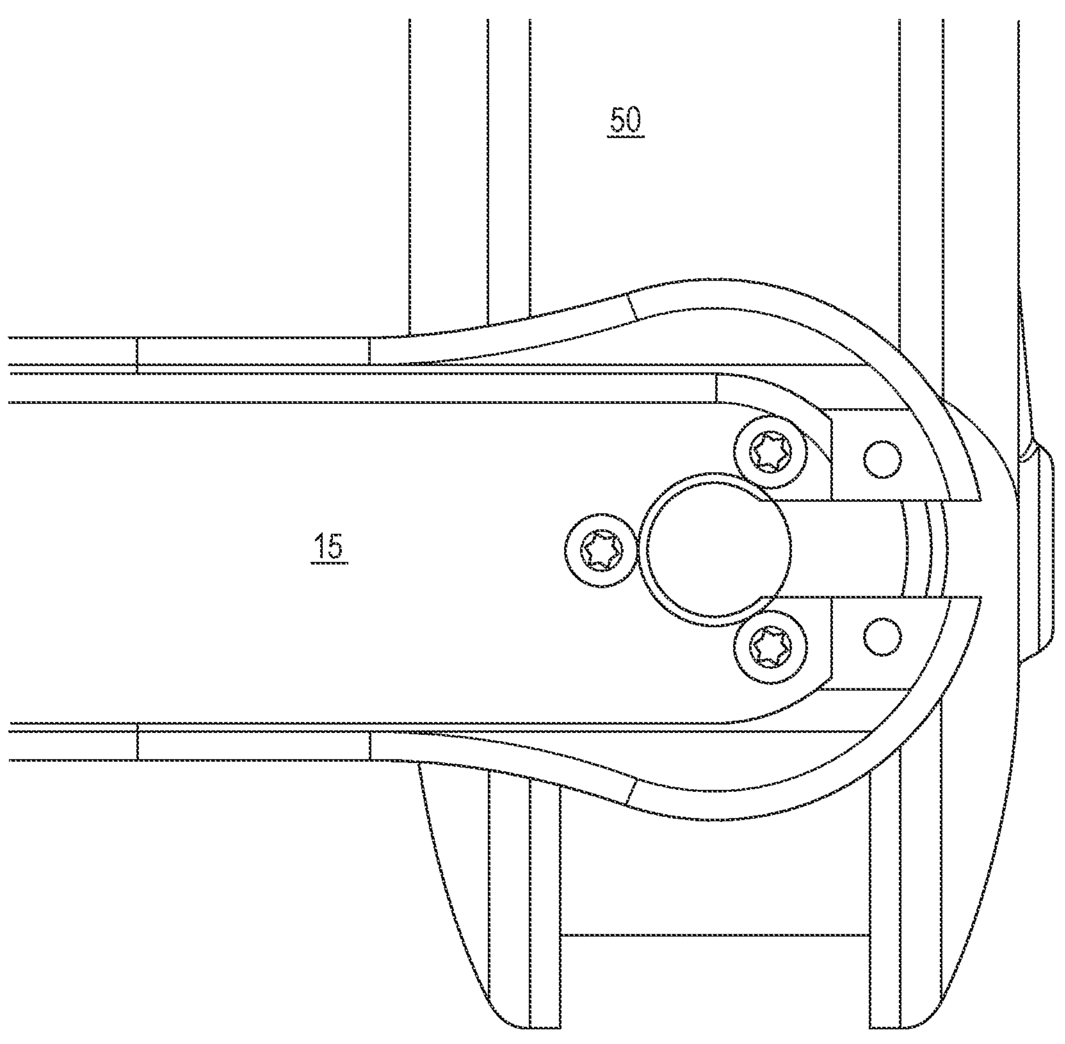
Figure 6A:
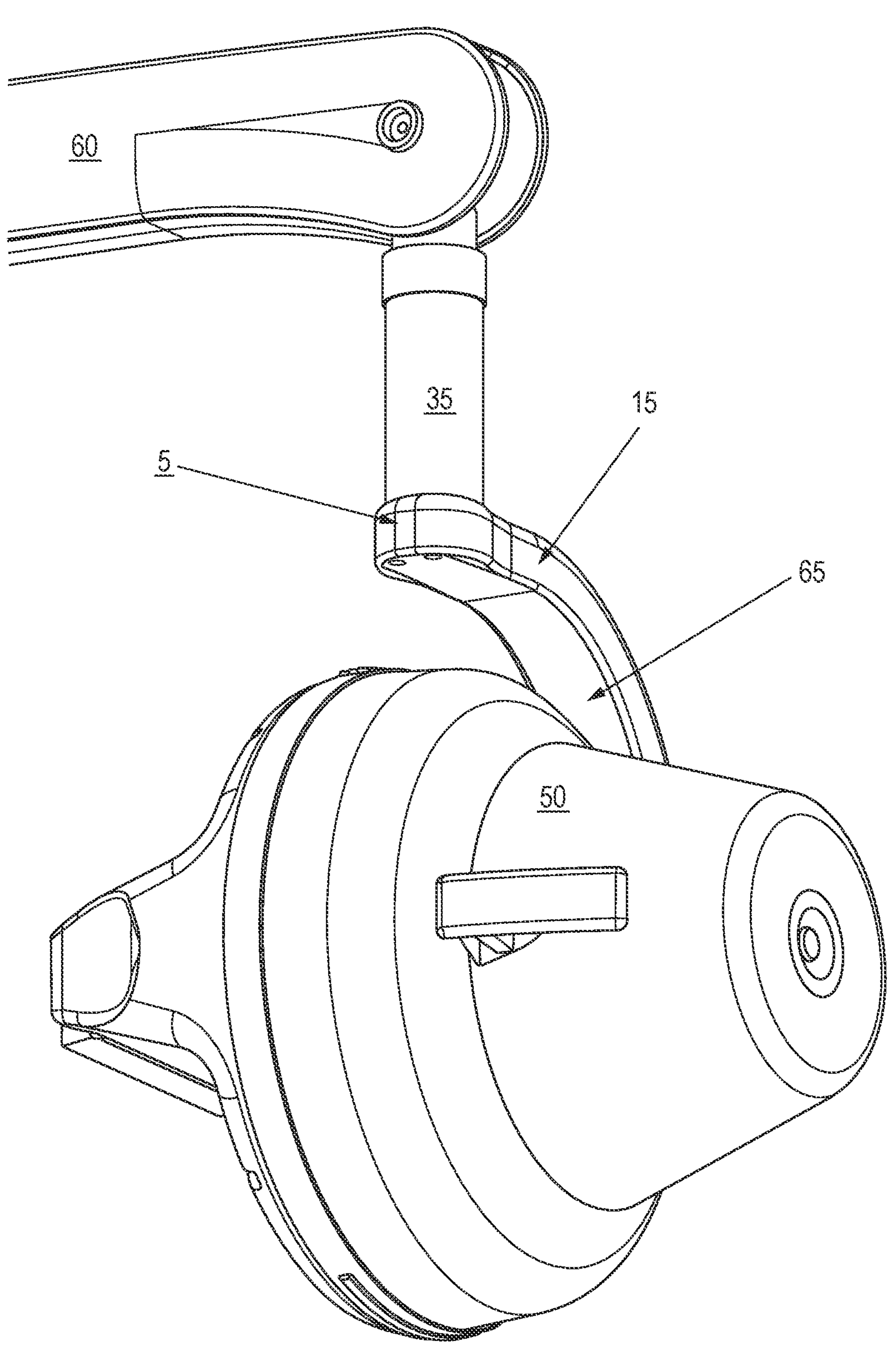
FIGS. 6A, 6B, and 6C show some embodiments of a process for disconnecting an X-ray head from the remainder of an X-ray imaging system.
Figure 6B:
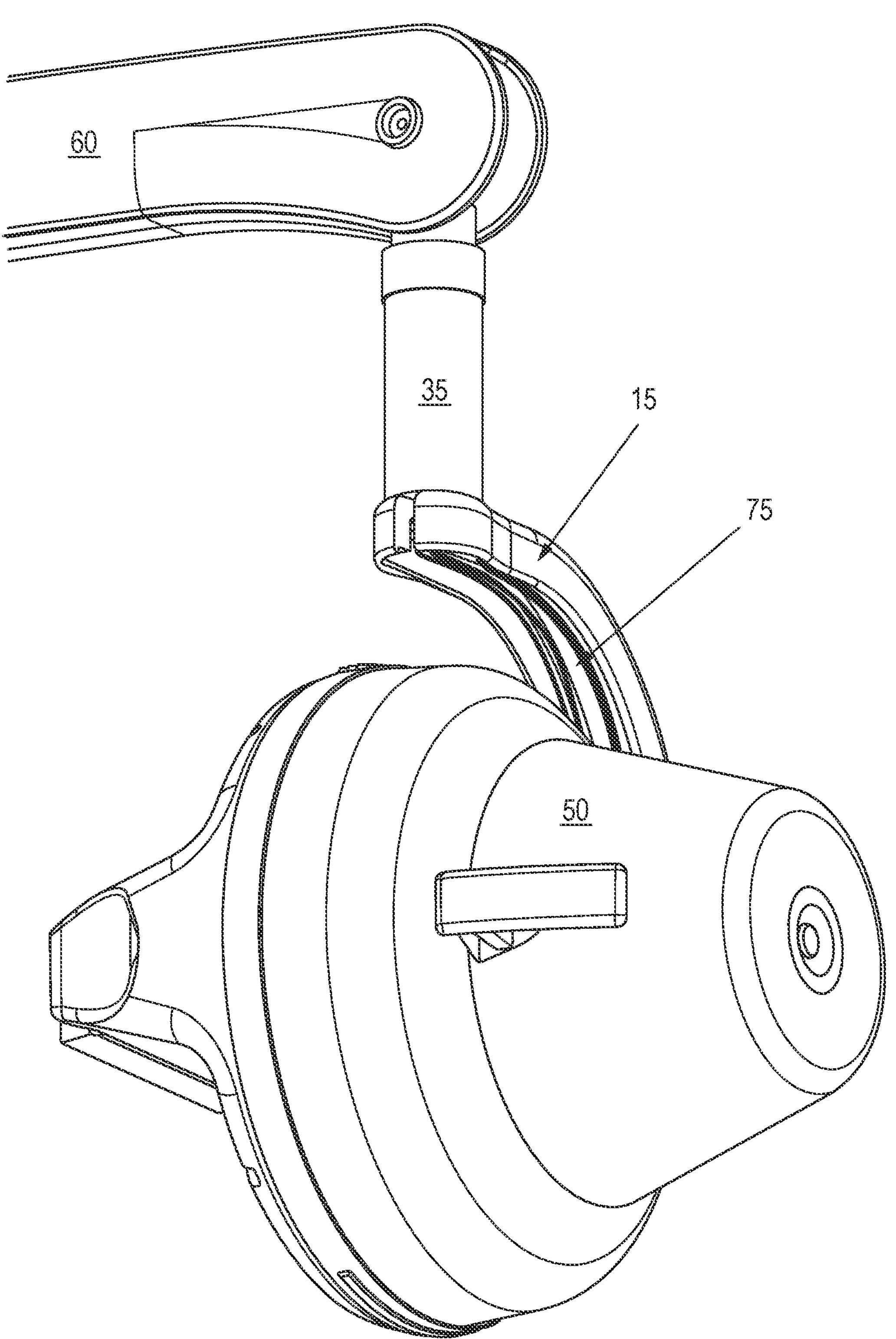
Figure 6C:
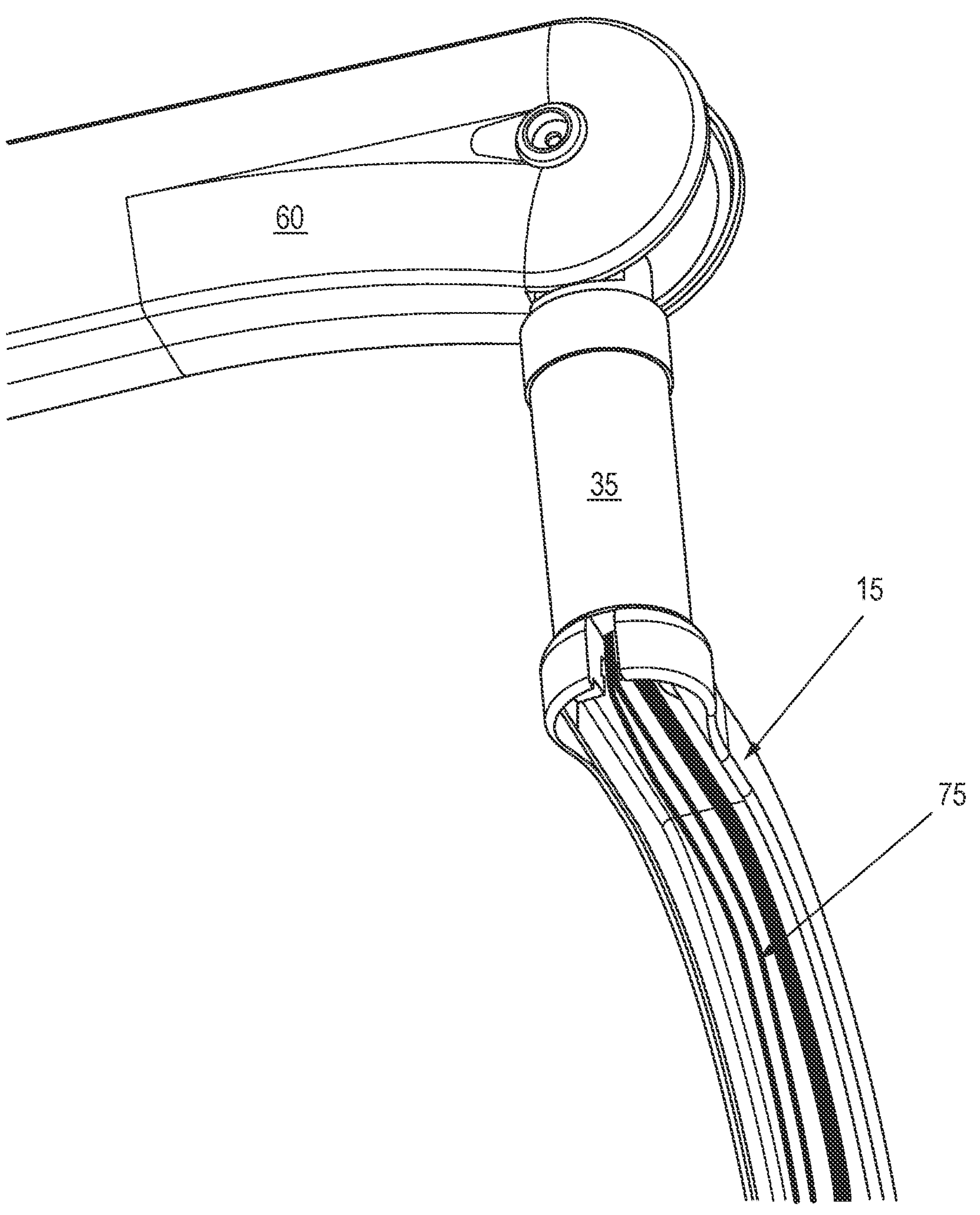

One example of the disconnect feature can be seen in FIGS. 4, 5, and 6A through 6C. As shown in FIG. 4 (perspective view) and FIG. 5 (bottom view), the underside 25 of the yoke 15 where the cabling 75 (not shown) will run is shown. As shown in FIGS. 6A-C, the upper part of the yoke 15 can be attached to the arm extension 35 of the arm 60. The cabling 75 can run from the X-ray head 50, along the underside of the yoke 15, and through the arm extension 35. A cover 65 can cover the underside of the yoke 25 and the cabling 75.

To remove the X-ray head 50, as shown in FIGS. 6A-C, the user or operator will need to remove the cover 65 from the underside of the yoke. This removal will expose the cabling 75, as shown in FIG. 6B. The cabling 75 can then be separated using the electrical connector, leaving part of the cabling 75 connected to the arm extension 35 and part of the cabling connected to the X-ray head 50. The last part of the disconnect process is then to disconnect the mechanical connection. This process involves removing the screws shown in FIGS. 4 and 5. With these screws removed, the X-ray head 50 and the yoke 15 can be removed from the X-ray system 10. The number of screws (or other mechanical connectors) that should be used should be kept to a minimum number to make the disconnection process simpler, quicker, and easier. However, a sufficient number of connectors must be used to provide the appropriate strength and reliability so that the X-ray system does not fail because of a weak mechanical connection. In some configurations, no more than 6 screws or connectors would be required in the application. In other configurations, 5 screws, 4 screws, 3 screws or perhaps even 2 screws or 1 screw could be sufficient provided that some kind of additional mechanical element such as a pin or some form of registration for the mechanical connection to provide stability is used.

The disconnect feature can be positioned at any point along the arm 60 or yoke 15 of the X-ray system 10. In some embodiments, the disconnect feature can be located between the yoke 15 and the X-ray head 50. In other embodiments, the disconnect feature can be located between the arm 60 and the yoke 15. These other embodiments would also include locating the disconnect feature between the arm extension 35 and the yoke 15. In yet other embodiments, the yoke can contain multiple parts (e.g., an upper part and a lower part) with the disconnect feature located between the multiple parts (e.g., between the upper part and lower part). Likewise, the arm can contain multiple parts (e.g., an upper part and a lower part) with the disconnect feature located between the multiple parts (e.g., between the upper part and lower part). An example of these embodiments including locating the disconnect feature between arm 60 and arm extension 35 is shown in FIG. 2. In still other embodiments, the cabling can include an upper portion that is coupled to the control device 85 and a lower portion that is coupled to the high voltage electronics in the X-ray head and the disconnect feature is positioned between the upper portion and the lower portion such that when disconnected, the X-ray head can be removed while still coupled to the lower portion. The electrical connector and the mechanical connector of the disconnect feature can be located in different places on the arm and/or yoke or they can be located in substantially the same location.

The disconnect feature should also be configured so that the mechanical and electrical disconnects are easy to operate by any user, including an untrained user. This ability can be obtained by using common electrical connectors so that an untrained user (i.e., one that is familiar with the types of electrical connectors commonly used within computers and other similar electronic devices) will be able to operate the electrical disconnects. Similarly, common mechanical connectors such as screws, nuts and bolts, clips, and other mechanical fastening devices can be used for the mechanical disconnects for easy connection and disconnection. Where this is not possible and more complex disconnects are used, instructions can be provided for how to use and operate the disconnect feature.

Figure 8:
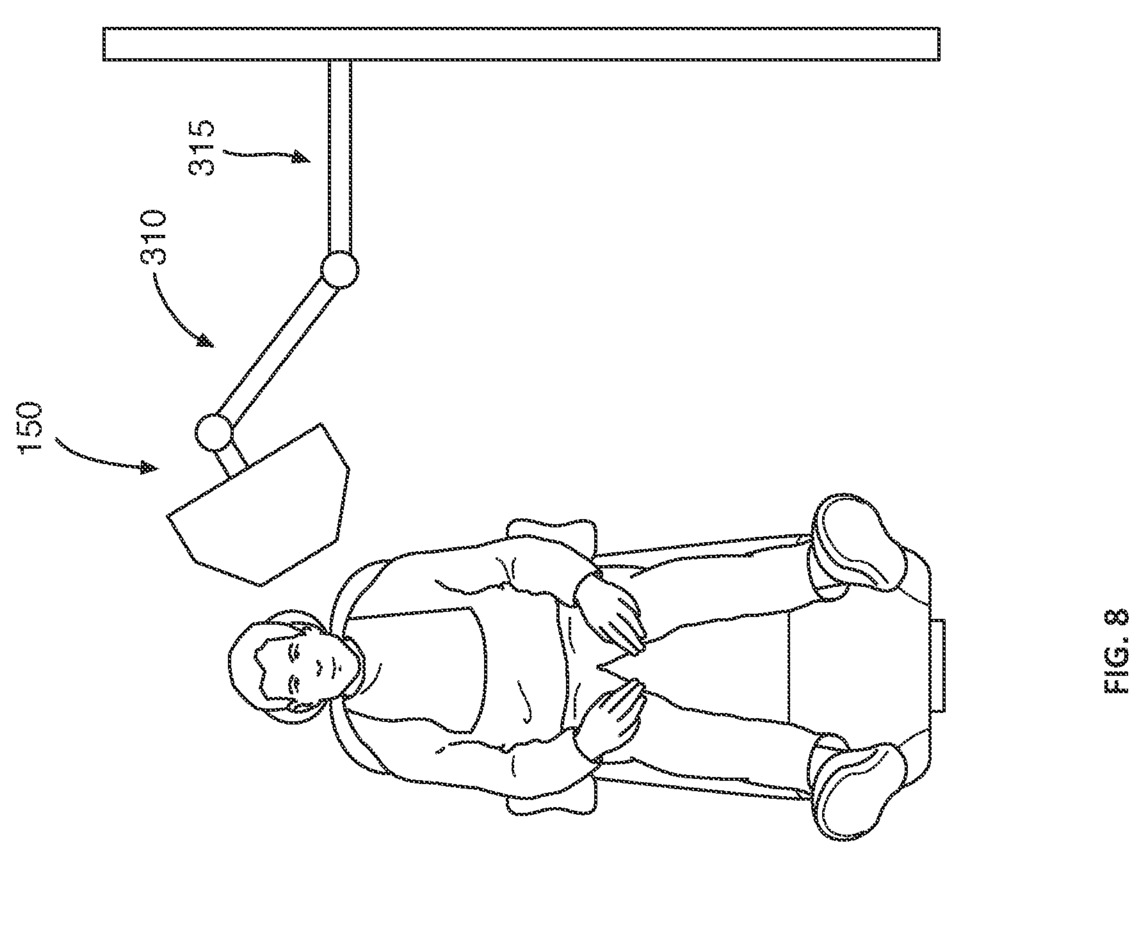
FIGS. 7 and 8 shows some embodiments X-ray imaging systems used for dental imaging.
Figure 7:
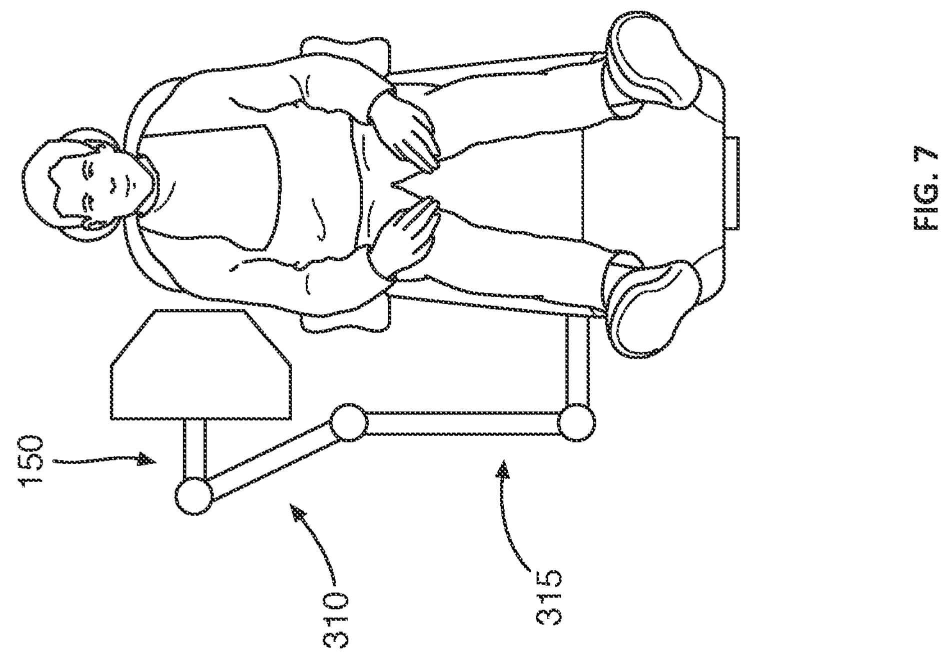

In some embodiments, the X-ray system 10 can be mounted to a wall or a chair, as depicted in FIGS. 7 and 8. In other embodiments, the X-ray imaging system may be a mobile system mounted on a wheeled base structure (like a cart) that can be moved from site to site for use. In these configurations, it is desirable that the X-ray system should be as small and light as possible while still providing the imaging capability. Accordingly, the size and weight of the X-ray head 50 should be limited so that the X-ray head 50 can be easily disconnected from the rest of the X-ray system 10. If the X-ray head 50 is too heavy or too big, it can't be disconnected quickly and easily by an average operator. In some embodiments, the X-ray head 50 fits within a rectangular volume of less than about 50 cm× about 50 cm× about 60 cm and weighs less than about 15 Kg. In other configurations, the X-ray system can be smaller than about 35 cm×35 cm×40 cm and weigh less than about 10 Kg. In other embodiments, the X-ray head 50 fits within a rectangular volume of less than about 25 cm× about 25 cm× about 30 cm and weighs less than about 5-6 Kg. If it is larger or heavier than these amounts, it would be difficult to be wall mounted as shown in FIG. 8 or chair mounted as shown in FIG. 7, as well as being too bulky or heavy for mobile system. As well, when it is larger and heavier, it can be difficult to position for the operator and it could increase patient anxiety.

In some embodiments where the X-ray imaging system is a mobile system, the constraints on weight of the X-ray system and the size or volume of the X-ray head are even more restrictive. This situation occurs because the X-ray system will be typically mounted at the end of an arm 60 and the weight of the X-ray head 50 and the arm 60 will need to be balanced by the size of the base of the mobile system and the weight on the base. Thus, additional weight on the X-ray head 50 will also require additional weight (stronger structural members, etc.) in the arm 60. This will result in additional weight to the mobile base, indicating that any weight added to, or conversely removed from, the X-ray head will have a multiplier effect on the over-all X-ray system weight and ease of movement and positioning.

To help reduce the size and weight of the X-ray head to meet these requirements, the X-ray head can be configured with power supplies and other electrical components located outside of head. The components retained within the head can be selected with the overall weight in consideration, such as the physical size and weight of the motor that drives the rotational stage, whether a ventilation fan is required, and/or the materials of the components. For example, the X-ray head can be made from lightweight materials such as aluminum and excess material can be machined or cut away to reduce weight. In some configurations, the X-ray head could be configured to reduce the extension of the main support beam to only reach the center of the head, as shown in X-ray head 450 of FIG. 11, as well as using lighter materials and structures to support the cover and other components beyond the main support. These sizes and weights enable a single, average-size user to disconnect and/or connect the X-ray head to the rest of the X-ray system without additional assistance that would otherwise be required to support a heavier device during the disconnect/reconnect procedure. This smaller size and weight also enables cheaper and easy shipping of the X-ray head to a remote location for repair, as well as easier installation.

As described herein, the cabling 75 used in the X-ray system 10 is designed for low voltages and low currents in some configurations. Using low voltages and low currents in the cabling 75 simplifies the electrical connectors and makes all of the assembly smaller, and the wires thinner and more flexible. In these configurations, most of the electrical signals carried in the cabling 75 will be for control and data transmission and only the lines that provide power to the X-ray head, while still low voltage and lower current, will need to carry an amp or more of current. Thus, the high-voltage power to create the X-rays will only be generated within the X-ray head itself using the low voltage and low current power carried by the cabling 75. This permits the X-ray system 10 in these configurations to be both mobile and portable by reducing weight required for heavier cabling, as well as eliminating the need to have any high-voltage cabling with the thick and stiff electrical insulation required to resist high-voltage arcs in the arm 60.

The X-ray systems described herein exhibit several helpful features. One helpful feature includes the ability to quickly and easily remove the X-ray head from the rest of the imaging system. This allows the X-ray head to be quickly replaced, reducing the downtime for the X-ray imaging system during repair. As well, this allows the X-ray head (a relatively light component) to be moved without having to move the rest of the X-ray system which is relatively heavier. For example, the X-ray head could be removed and easily shipped to a properly equipped, centrally-located repair facility for repair without shipping the rest of the X-ray system. As well, a single X-ray head could be used with multiple X-ray systems that are in a fixed location.

A second helpful feature is the ability to assemble the X-ray head 50 separate of the X-ray system 10 and test it. This capability allows the X-ray head 50 to be removed and shipped for repair separate from the rest of the X-ray system 10. This feature also allows a replacement X-ray head 50 to be shipped to the user's site as soon as a notice of a problem is received, reducing downtime for the X-ray system 10 when the X-ray head 50 is not functioning and needs repair. This ability to implement a repair at the user's site by providing a replacement X-ray head and shipping the non-functional head to a central repair location provides significant cost reductions by reducing or even eliminating the need to pre-position service personnel at strategic locations around the country, reduces the need to pay for travel of service personnel, reduces the need to pre-position parts and material, and provides other benefits. It also benefits the user's clinic or organization because they have less down-time due to equipment being non-serviceable or unavailable, leading to more productive time meeting the needs of patients, less re-scheduling of patients due to unavailable equipment, etc. And by designing the system so that the X-ray head (the most complex and most failure-prone part of the X-ray imaging system) can be quickly and easily removed and replaced using basic tools and basic technical repair skills keeps the X-ray imaging operating as long as possible and repair becomes less difficult and requires less resources for both the manufacturer and the user.

A third helpful feature is that the X-ray head 50 can be configured to be modular. Thus, it can be easily disconnected from a first X-ray system (such as a wall-mounted system) and then connected to a second X-ray system (such as a system mounted near a dental chair). This feature reduces the overall costs of the system, while also maintaining flexibility and usability.

Finally, by having a low weight, small size, quick and easy connection/disconnection, it is easy and quick to ship the X-ray head for off-site repair. Thus, the X-ray systems are easier to service, have lower costs, and provide more uptime (and less downtime) for the operator relative to some other conventional X-ray systems.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An X-ray imaging system, comprising:

an X-ray head containing a rotating X-ray source and supporting electronics;

a control device;

an arm coupled to the X-ray head; and electrical cabling disposed within the arm and configured to connect the supporting electronics to the control device, the cabling comprising a disconnect between the supporting electronics and the control device;

the X-ray head removably attached to the arm so that when the electrical cabling is disconnected, the X-ray head can be removed from the X-ray system.

2. The X-ray imaging system of claim 1, wherein the arm further comprises a yoke connected to the X-ray head.

3. The X-ray imaging system of claim 2, wherein the yoke is further configured to also be mechanically disconnected from the X-ray head.

4. The X-ray imaging system of claim 1, wherein the electrical cabling comprises an upper portion coupled to the control device and a lower portion coupled to the remainder of the X-ray imaging system.

5. The X-ray imaging system of claim 1, wherein the X-ray head comprises high voltage electronics and the electrical cabling operates with a low voltage.

6. The X-ray imaging system of claim 1, further comprising:

an X-ray detector located on an opposite side of an object to be imaged than the X-ray source, the X-ray detector used with the X-ray source to capture images of the object.

7. The x-ray imaging system of claim 6, wherein the supporting electronics synchronize the x-ray detector with the x-ray source so that the system can capture multiple x-ray images while the x-ray source rotates.

8. The system of claim 1, wherein the object is a single tooth or multiple teeth.

9. An X-ray imaging system, comprising:

an X-ray head containing a rotating X-ray source and high voltage electronics;

a control device;

a yoke connected to the X-ray head;

an arm coupled to the yoke; and electrical cabling disposed within the arm and configured to connect the high voltage electronics to the control device, the cabling comprising a disconnect between the supporting high voltage electronics and the control device;

the X-ray head removably attached to the yoke so that when the electrical cabling is disconnected, the X-ray head can be removed from the X-ray system.

10. The X-ray imaging system of claim 9, wherein the yoke is further configured to also be mechanically disconnected from the X-ray head.

11. A method for repairing an X-ray system, comprising:

providing an X-ray imaging system with an X-ray head containing a rotating X-ray source and high voltage electronics, a control device, a yoke connected to the X-ray head, an arm coupled to the yoke, and electrical cabling running from the control device, through the arm and the yoke, and into the X-ray head;

disconnecting the X-ray head from the remainder of the X-ray system; and repairing the X-ray head while the X-ray head is disconnected.

12. The method of claim 11, further comprising reconnecting the X-ray head after the X-ray head has been repaired.

13. The method of claim 11, comprising disconnecting the X-ray head by disconnecting the yoke from the arm.

14. The method of claim 11, wherein the disconnection is both a disconnection in the electrical cabling and a mechanical disconnection.

15. The method of claim 11, wherein the electrical cabling operates with a low voltage.

* * * * *